(12) United States Patent
Sutton et al.

(10) Patent No.: US 7,179,232 B2
(45) Date of Patent: Feb. 20, 2007

(54) CONTROLLED ORIFICE SAMPLING NEEDLE

(75) Inventors: Jeffrey Karl Sutton, Medway, MA (US); John C. Voellmicke, Cumberland, RI (US)

(73) Assignee: Depuy Acromed, Inc., Raynham, MA (US)

( * ) Notice: Subject to any disclaimer, the term of this patent is extended or adjusted under 35 U.S.C. 154(b) by 425 days.

(21) Appl. No.: 10/608,774

(22) Filed: Jun. 27, 2003

(65) Prior Publication Data

US 2004/0267154 A1 Dec. 30, 2004

(51) Int. Cl.
*A61B 10/00* (2006.01)

(52) U.S. Cl. ........................ 600/567; 600/562
(58) Field of Classification Search ............... 600/567, 600/562, 564; 606/159
See application file for complete search history.

(56) References Cited

U.S. PATENT DOCUMENTS

| | | | |
|---|---|---|---|
| 4,605,011 A | 8/1986 | Naslund | |
| 5,098,411 A * | 3/1992 | Watson et al. | 604/268 |
| 5,395,317 A | 3/1995 | Kambin | |
| 5,515,861 A | 5/1996 | Smith | |
| 5,603,703 A * | 2/1997 | Elsberry et al. | 604/268 |
| 5,810,826 A * | 9/1998 | .ANG.kerfeldt et al. | 606/80 |
| 6,280,399 B1 | 8/2001 | Rossin et al. | |
| 6,488,636 B2 * | 12/2002 | Bryan et al. | 600/566 |
| D489,456 S | 5/2004 | Krueger et al. | |
| 6,733,479 B1 * | 5/2004 | Ott | 604/264 |
| 6,755,793 B2 | 6/2004 | Lamoureux et al. | |
| 2002/0016555 A1 * | 2/2002 | Ritchart et al. | 600/567 |
| 2002/0042581 A1 * | 4/2002 | Cervi | 600/567 |
| 2002/0082519 A1 * | 6/2002 | Miller et al. | 600/566 |
| 2002/0193705 A1 * | 12/2002 | Burbank et al. | 600/562 |
| 2003/0009132 A1 * | 1/2003 | Schwartz et al. | 604/152 |
| 2003/0050574 A1 * | 3/2003 | Krueger | 600/567 |
| 2003/0093008 A1 * | 5/2003 | Van Bladel et al. | 600/567 |
| 2004/0249306 A1 | 12/2004 | Islam | |

FOREIGN PATENT DOCUMENTS

WO    WO 02/083228    10/2002

\* cited by examiner

*Primary Examiner*—Max F. Hindenburg
*Assistant Examiner*—Kristin D Rogers

(57) ABSTRACT

A bone marrow sampling device is provided, including an outer cannula having a sidewall with a plurality of openings and a distal tissue penetrating tip. An inner cannula is positioned within the outer cannula, and includes a sidewall with at least one opening. Selective relative movement of the inner cannula and the outer cannula enables the device to be configured in multiple bone marrow sampling modes in which the at least one opening in the sidewall of the inner cannula is aligned with different openings in the sidewall of the outer cannula such that bone marrow can be drawn into the inner lumen of the inner cannula from different radial and longitudinal positions external to the sidewall of the outer cannula without the need to reposition the outer cannula.

18 Claims, 7 Drawing Sheets

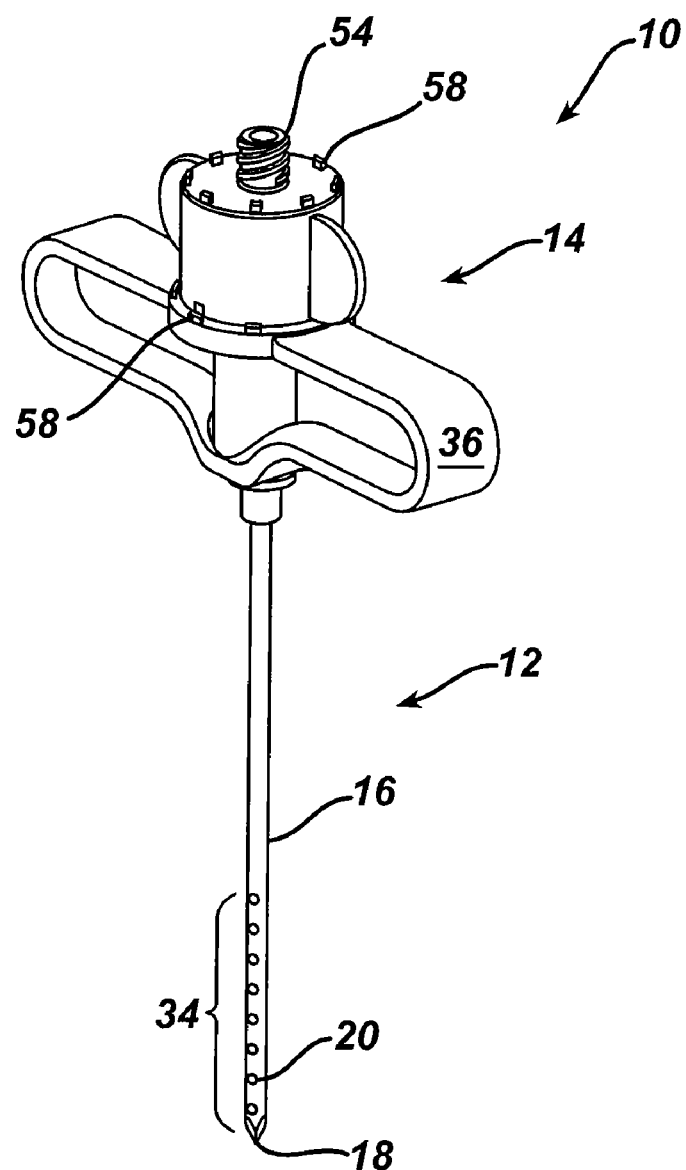

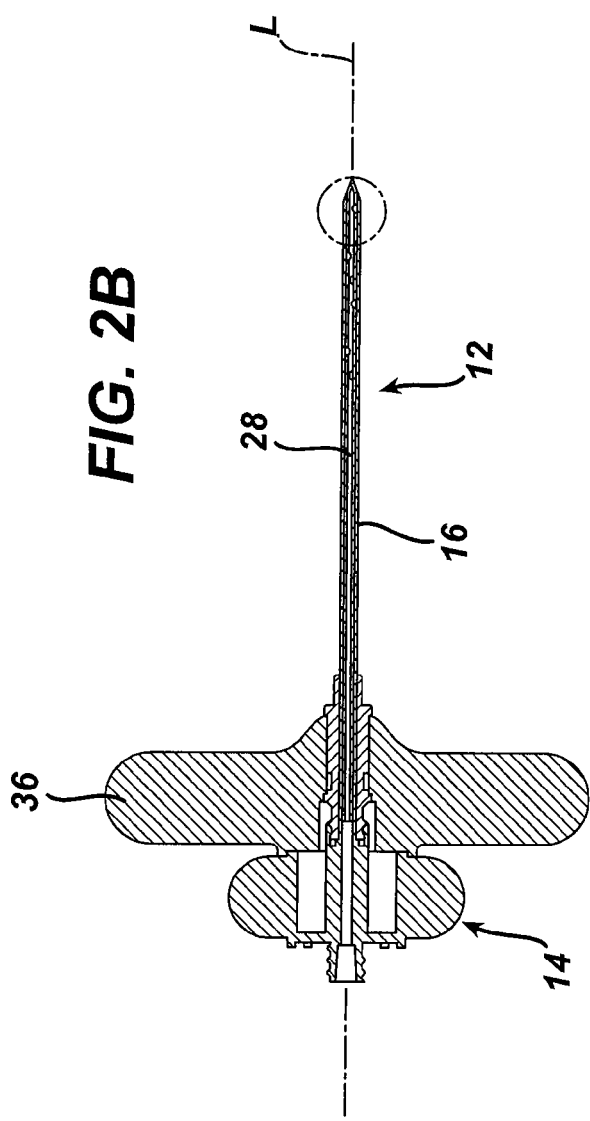
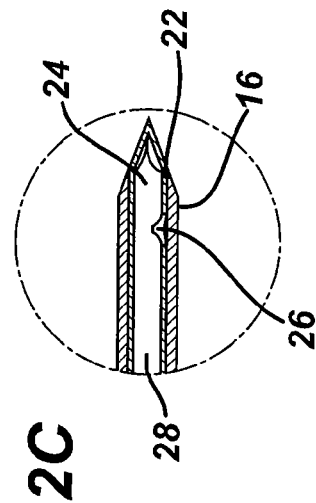
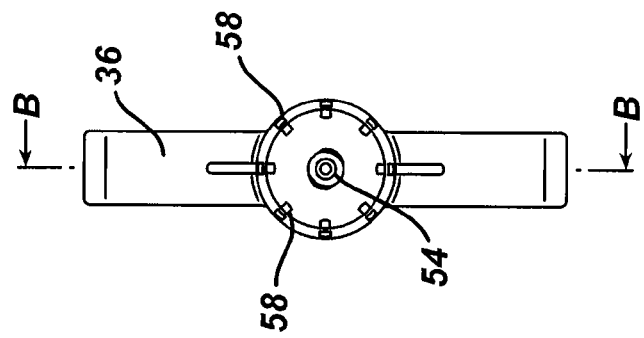

CONTROLLED ORIFICE SAMPLING NEEDLE

FIELD OF THE INVENTION

The present invention relates to sampling devices and procedures, and particularly bone marrow sampling devices, which selectively sample from multiple sites without the need to reposition the sampling device.

BACKGROUND OF THE INVENTION

Bone marrow sampling procedures are commonly performed to diagnose various conditions that affect the different types of blood cells, to diagnose certain cancers to determine the extent of the cancer, and to obtain marrow for transplantation and/or graft preparation. The most frequent site for obtaining bone marrow is through the pelvic bone, known as the ilium. A portion of this bone is readily accessible in most people from the lower back and is usually marked by shallow dimples on either side of the spine. Other aspiration sites include the front of the pelvic bone, near the groin, and the sternum.

A bone marrow aspiration procedure typically involves passing a bone marrow aspiration needle through the skin and soft tissue and into the bony cortex where the needle enters the spongy bone containing the bone marrow. Once the needle is positioned in the spongy bone, a syringe or other fluid-withdrawing device is attached to the proximal end of the device and is used to draw bone marrow from the distal end of the needle.

Once the marrow in the immediate vicinity of the distal end is collected, which occurs after a short period of time and before a full sample is collected, continued aspiration only withdraws plasma and fluid. To withdraw sufficient quantities of a bone marrow sample, it is often necessary to reposition the needle multiple times. Unfortunately, frequent repositioning of the needle can cause damage to the sampling area and result in patient pain and discomfort.

Accordingly, there is a need for a bone marrow aspiration and collection device which more efficiently acquires bone marrow samples while minimizing any associated patient pain and discomfort.

SUMMARY OF THE INVENTION

The present invention relates to a bone marrow sampling device having an outer cannula and an inner cannula. The outer cannula has a sidewall defining a inner lumen and a closed distal end with a tissue penetrating tip, and the sidewall has a plurality of openings formed therein that are spaced apart at different radial and longitudinal positions. Each of the plurality of openings is in fluid communication with the inner lumen of the outer cannula. The inner cannula likewise has a sidewall defining an inner lumen, and the inner cannula is adapted to be disposed within and mated to the outer cannula such that the outer cannula and inner cannula are selectively moveable with respect to each other. The inner cannula also has at least one opening formed in the sidewall.

Selective relative movement of the inner cannula and the outer cannula enables the device to be configured in multiple bone marrow sampling modes in which the at least one opening in the sidewall of the inner cannula is able to be aligned with different openings in the sidewall of the outer cannula such that bone marrow can be drawn into the inner lumen of the inner cannula from different radial and longitudinal positions external to the sidewall of the outer cannula without changing the position of the outer cannula. Thus selective relative movement between the inner cannula and the outer cannula can change the location of the withdrawal aperture by aligning different openings in the inner and outer cannulae. The present invention is advantageous for fluid sampling procedures (e.g., bone marrow sampling) because it enables a physician to withdraw bone marrow samples from various locations in a sampling area without having to reposition the sampling device. Once the supply of bone marrow adjacent a first withdrawal aperture is removed, a physician can manipulate the device to close the unproductive withdrawal aperture and open a second withdrawal aperture in a different area, thereby changing the sampling location without repositioning the device.

The relative movement between the inner and outer cannulae can be rotational, translational, or both rotational and translational. In one embodiment, the selective relative movement between the two cannulae may be automated. Markings on the inner and outer cannula may also be used to provide an indication when the at least one opening on the inner cannula lines up with a selected opening on the outer cannula to create a withdrawal aperture.

In another embodiment, a second inner cannula may be disposed between the inner and outer cannulae. The second inner cannula can provide an additional degree of freedom, thus increasing the surgeon's options to control the opening and closing of withdrawal apertures. The second inner cannula may have at least one opening in its sidewall, or it may have a solid outer sidewall that is free of openings. When the second inner cannula is moved with respect to the inner cannula and the outer cannula, such movement is effective to close or open withdrawal apertures between the inner and outer cannula.

In yet another embodiment, the second inner cannula may have a channel in its outer sidewall that can provide a channel for delivering liquid to an area adjacent the device. The channel allows a physician to provide liquids, such as saline solution, a drug and/or a bioactive solution.

BRIEF DESCRIPTION OF THE DRAWINGS

FIG. 1 is a perspective view of one embodiment of a controlled orifice sampling needle according to the present invention;

FIG. 2A is a top view of the device shown in FIG. 1;

FIG. 2B is a cross sectional view along the line B—B in FIG. 2A;

FIG. 2C is a detailed view of the distal end of the device shown in FIG. 2B;

DETAILED DESCRIPTION OF THE INVENTION

The present invention relates to a bone marrow sampling device which can be configured in multiple bone marrow sampling modes to enable samples to be withdrawn from different areas without having to reposition the device within a patient. The desired bone marrow sampling mode is achieved by selectively opening and closing certain apertures in a sampling cannula so that the active withdrawal aperture is selectively positioned at a location on the device adjacent to a bone marrow rich sampling area.

Figure 3:
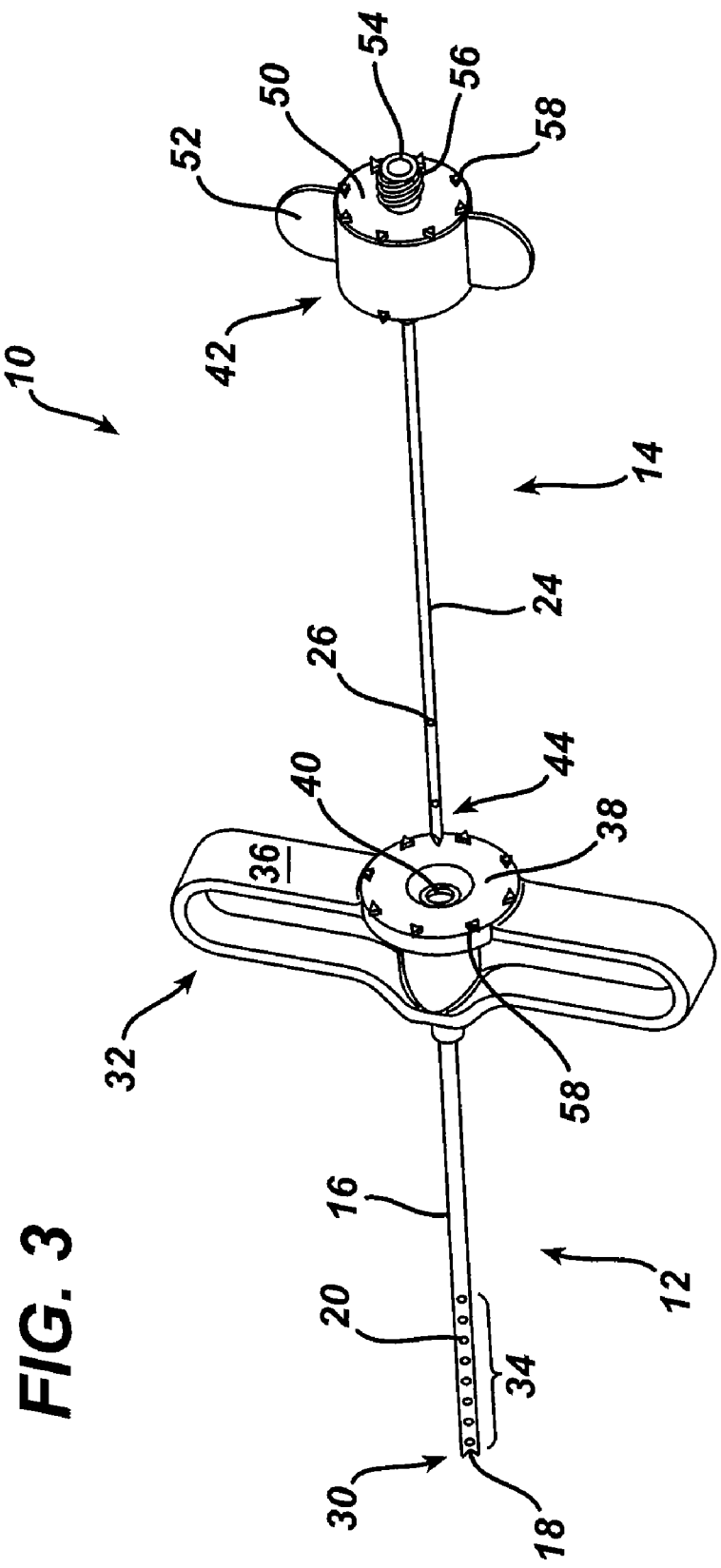
FIG. 3 is a disassembled view of the controlled orifice sampling needle in FIG. 1.

As shown in FIGS. 1–3, the bone marrow sampling device 10 of the present invention comprises an outer cannula assembly 12 and an inner cannula assembly 14 which is positionable within and movable with respect to the outer cannula assembly 12. The outer cannula assembly includes an elongate cannula 16 having a tissue penetrating distal tip 18. A plurality of openings 20 are formed in the wall of the outer cannula 16 and extend into an inner lumen 22 (FIGS. 2B and 2C) of outer cannula 16. The inner cannula assembly 14 includes a inner cannula 24 having one or more openings 26 leading to an inner lumen 28. The sampling device 10 can be configured in multiple bone marrow sampling modes in which one or more openings 28 of the inner cannula 24 are aligned with one of the openings 20 of the outer cannula 16 to enable sample (e.g., bone marrow) collection.

The device 10 is particularly advantageous, because samples can be withdrawn from different regions without having to reposition the device. For example, a surgeon can collect the available bone marrow cells in a region adjacent to a first withdrawal aperture, and when the supply of available bone marrow cells have been depleted from that region, the first withdrawal aperture can be closed and second withdrawal aperture opened by selectively moving the inner and outer cannula assemblies relative to one another. By switching to a second withdrawal aperture, a larger sample can be collected without the additional patient discomfort caused by repositioning the sampling needle.

With further reference to FIG. 3, which illustrates a disassembled view of device 10, the outer cannula assembly 12 has a distal portion 30 a proximal portion 32, and a cannula shaft 16 having multiple openings 20 in the sidewall thereof. As noted above, the distal portion 30 includes a distal tissue penetrating tip 18 capable of penetrating soft tissue and bone. The tissue penetrating tip 18 can have a variety of configurations, but in an exemplary embodiment it can be formed of three triangle-shaped surfaces that meet at an apex. A person skilled in the art will appreciate that the tissue penetrating tip can have virtually any alternative configuration, but preferably it is a closed penetrating tip.

The cannula shaft 16 is a hollow, elongate member having multiple openings 20 in a sidewall thereof. Each opening communicates with a lumen 28. The outer diameter of the cannula shaft 16 should be of such size that it is able to penetrate patient tissue without undue discomfort or damage to the tissue. Further, the inner diameter of the cannula shaft 16 should be of sufficient size to accept the cannula shaft 24 of inner cannula assembly 14. In an exemplary embodiment, the outer diameter of cannula shaft 16 is in the range of about 0.7 to 6 mm, and more preferably from about 2 mm to 4 mm.

The inner diameter of cannula shaft 16 may be in the range of about 0.5 mm to 5.5 mm, and more preferably about 1.0 mm to 3.5 mm.

The openings 20 in the sidewall of the cannula shaft 16 provide an entrance for bone marrow cells and should have dimensions sufficient to limit damage to bone marrow cells as they are drawn into the device. In addition, properly sized openings reduce the chances of clogging the device. Preferably, the openings 20 have an open surface area in the range of about 0.5 $mm^2$ to 8 $mm^2$, and where the openings are circular, the diameter of the openings may be in the range of about 0.5 mm to 3 mm. Although the openings 20 are illustrated as circular, one skilled in the art will appreciate that the openings 20 could have any shape, such as, irregular, oval, rectangular, triangular, or any other shape through which bone marrow cells could travel.

The region of the cannula shaft 16 where the openings 20 are located defines the active area 34 of the cannula shaft 16. The openings 20 may extend along the entire length of the cannula shaft 16, or, as shown in FIG. 3, the active area 34 may be limited to the distal portion of the cannula shaft 16. In one embodiment, the active area 34 extends in a proximal direction from the distal end of the cannula shaft 16 for a distance in the range of about 3 cm to 10 cm, and even more preferably in the range of about 4 cm to 7 cm.

Each of the openings 20 in the active region 34 represent a possible withdrawal aperture for sampling bone marrow cells. Preferably, the number of opening 20 in the cannula shaft 16 can be in the range of about 1 to 20, and even more preferably in the range of about 2 to 12. Although a withdrawal aperture can be created through any of the openings 20 by aligning the opening 20 with an opening 26 on the inner cannula shaft 24, the total number of withdrawal apertures open at one time is preferably in the range of about 1 to 8.

Figure 5:
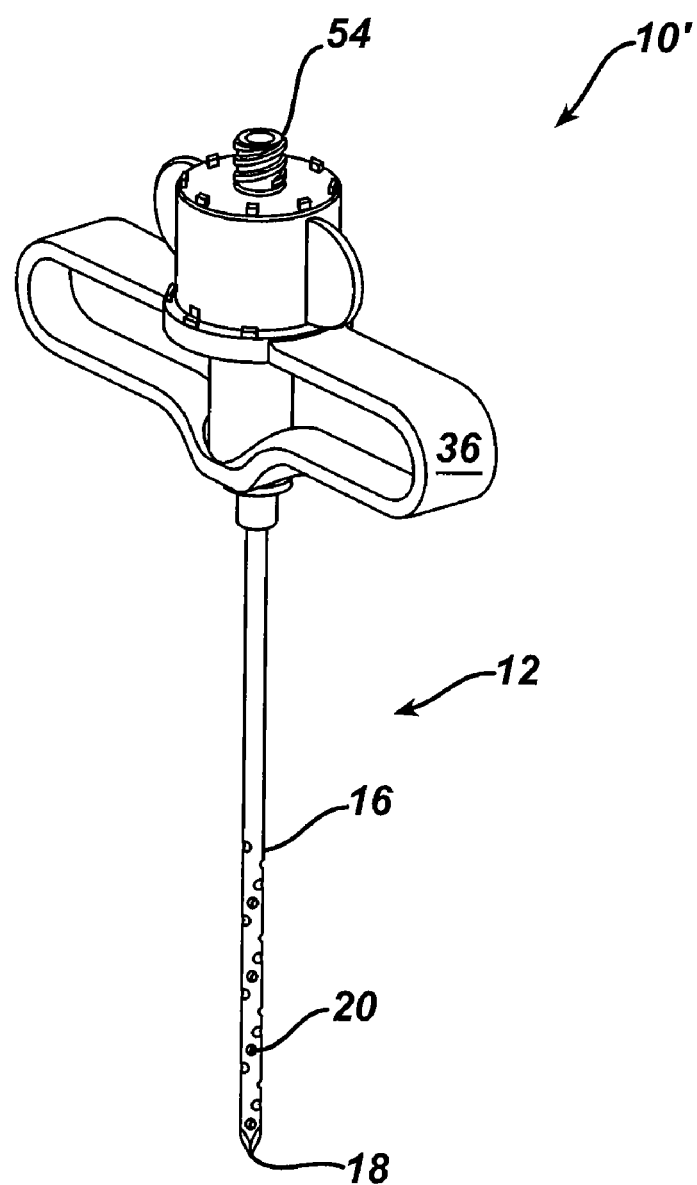
FIG. 5 is a perspective view of another embodiment of the controlled orifice sampling needle according to the present invention.
Figure 6C:
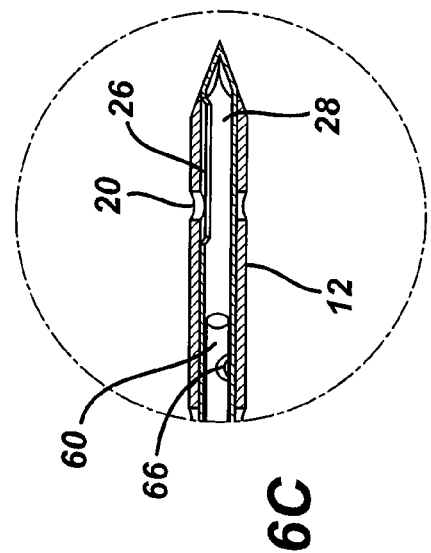
FIG. 6C is an enlarged view of the distal end of the device shown in FIG. 6A.
Figure 6B:
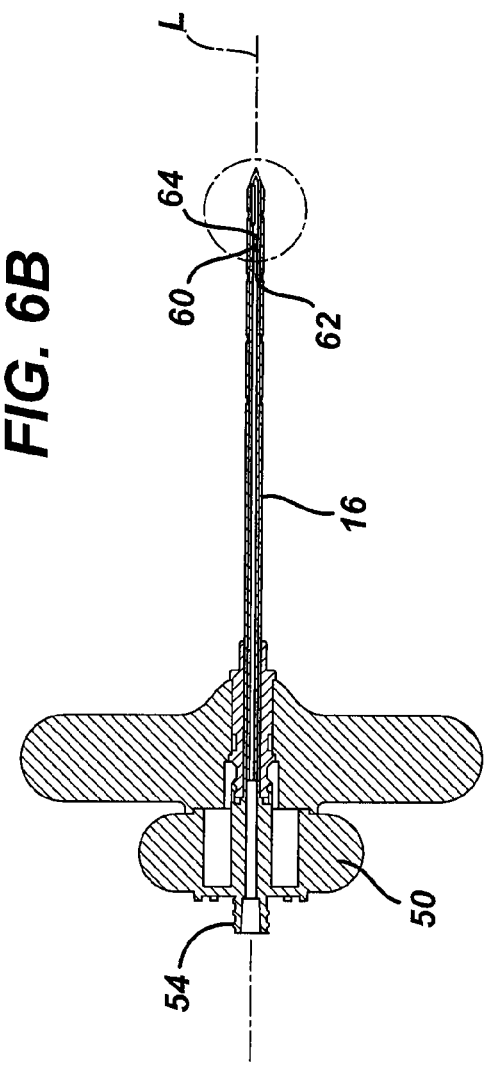
FIG. 6B illustrates a cross sectional view along the line B—B in FIG. 6A.
Figure 6A:
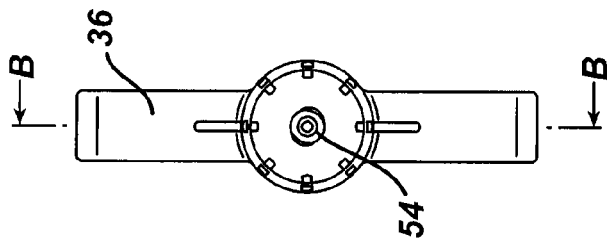
FIG. 6A is a top view of the device shown in FIG. 5.
Figure 7:
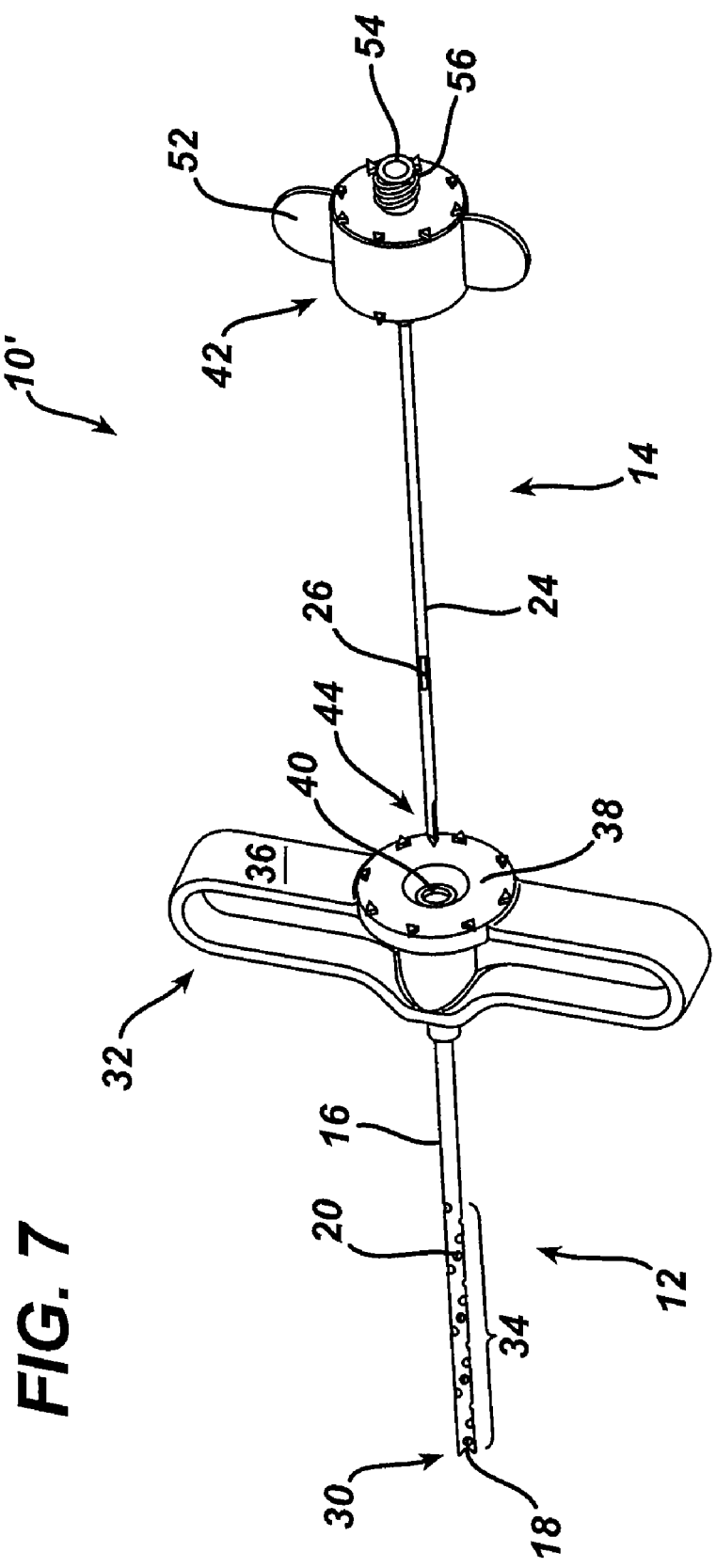
FIG. 7 is a disassembled view of the controlled orifice sampling needle shown in FIG. 5.

The openings 20 in the sidewall of the outer cannula shaft 16 may be radially and longitudinally spaced from one another along the cannula shaft 16 in a variety of patterns. In one embodiment, the openings 20 in the cannula shaft 16 are preferably uniformly distributed in the active region 24. By way of example only, FIGS. 1–3 illustrate a linear pattern of openings while FIGS. 5–7 illustrate a helical pattern. Further, the distance between openings can also vary, but they should be spaced apart by a distance in the range of about 2 mm to 10 mm and, more preferably, by about 5 mm. A person skilled in the art will appreciate that other patterns can also provide the device 10 with useful sampling options.

Referring still to FIGS. 1–3, the proximal portion 32 of outer cannula assembly 12 preferably includes a handle 36. The handle 36 can have virtually any shape and size, but it is preferably formed from a rigid body having a shape to facilitate grasping thereof. The exemplary handle shown in FIG. 3 is generally rectangular in shape and oriented in a direction transverse to a longitudinal axis (L) of the outer cannula assembly 12.

The proximal portion of the outer cannula assembly 12 may also include a proximally facing mating surface 38 which has a port 40 formed therein to permit access to lumen 22. As will be described below, surface 38 can seat a portion of the inner cannula assembly 14 when the two cannula assemblies are mated together.

In one embodiment, the port 40 is substantially tapered or funnel-shaped to allow convenient insertion of inner cannula assembly 14 therein. In addition, the taper of the port 40 can be configured to cooperate with a portion of the inner cannula assembly 14 to provide an interference fit between the outer and inner cannula assemblies 12, 14. Other mating arrangements between the outer and inner cannula assemblies, which allow relative movement of the two components, are also possible. For example, the inner and outer cannula assemblies can also be mated with a snap fit which prevents translational movement, but allows rotational movement. Further, a tongue and groove mating arrangement is also possible, in which a groove can be formed on either of the inner or outer cannula assemblies 14, 12, to allow only translational movement of the two components.

The inner cannula assembly 14, as also shown in FIGS. 1–3, has a proximal portion 42, a distal portion 44 and an elongate cannula shaft 24 extending therebetween. The cannula shaft 24 is hollow and includes at least one opening 26 in a sidewall thereof that is in fluid communication with a lumen 28.

The opening(s) 26 formed in the cannula shaft 24 are adapted to be selectively aligned with one or more of the openings 20 of the cannula shaft 16 to create a withdrawal aperture to permit bone marrow sample and/or other fluid to be conveyed from an area outside of the device (adjacent one of openings 20) and into lumen 28. Thereafter, as discussed below, the sample can be withdrawn through the proximal portion 42 of cannula shaft 24. In one embodiment, the inner cannula shaft 24 can have more than one opening 26, and one or more withdrawal apertures can be created by selective relative movement between the inner cannula shaft 24 and the outer cannula shaft 16. FIG. 3 illustrates an inner cannula shaft 24 with more than one opening 26.

Figure 4A:
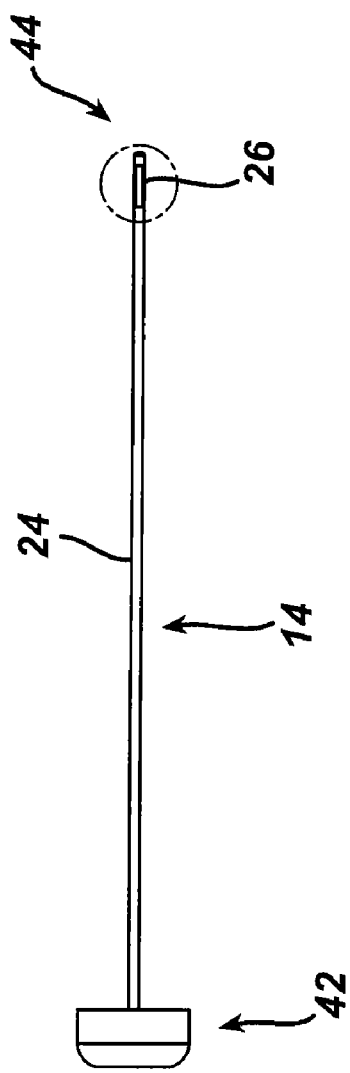
FIG. 4A is a side view of an inner cannula according to another embodiment of the invention.
Figure 4B:
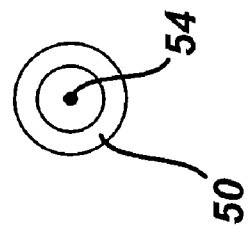
FIG. 4B illustrates a top view of the inner cannula shown in FIG. 4A.
Figure 4C:
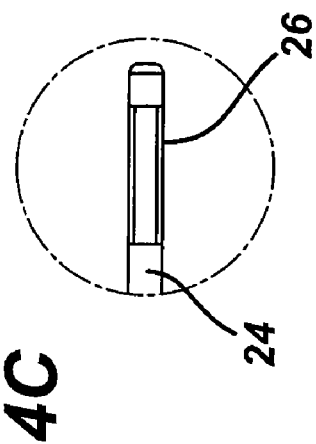
FIG. 4C is a detailed view of the distal end of the inner cannula shown in FIG. 4A.

In another embodiment, the inner cannula shaft 24 may have only one opening 26, which may be larger than openings 20, and which can be aligned with one or more openings 20 in the outer cannula shaft 16 by selectively moving the inner or outer cannula. FIGS. 4A–4C illustrate an inner cannula shaft 24 with only one larger, elongate opening 26 which can align with multiple openings 20 on the outer cannula shaft 16.

In use, the aspiration flow rate and/or pressure can be adjusted. For example, with the opening(s) 26 on the inner cannula shaft 24 fully aligned with an opening 20 on the outer cannula shaft 16, a maximum flow rate for the withdrawal aperture is achieved. To reduce the flow rate the, openings 26, 20 can be moved into partial alignment. The opening(s) 26 on the inner cannula shaft 24 may have a variety of shapes which facilitate adjustment of the aspiration flow rate. In one exemplary embodiment, the openings 26 may have an triangular shape so that when the opening 20 on the outer cannula shaft 16 is aligned with the peak of the triangular shaped opening 26, the aspiration is minimal. As the opening 20 is fully aligned with the center of the triangular shaped opening 26, the full aspiration flow rate is achieved. A person skilled in the art will appreciate that a variety of other openings 26 could provide an adjustable flow rate, including for example a series of progressively larger openings 26 which could be aligned with the opening 20 on the outer cannula shaft 16 to progressively increase or decrease the aspiration flow rate.

In any case, a person skilled in the art will further appreciate that the opening(s) 26 on the inner cannula shaft 24 can have a variety of shapes and sizes depending on the location of the openings 20 in the outer cannula shaft 16. Regardless of the number of openings 26 in the sidewall of the inner cannula shaft 24, the openings preferably have the same minimum size limitation as the openings 20 in the outer cannula shaft 16. That is, openings 26 should have a cross sectional area greater than about 2 mm$^2$.

The distal portion 44 of the inner cannula shaft 24 is adapted to fit within the outer cannula assembly 12 as shown in FIGS. 1–4C. The distal-most end of the distal portion 44 of the inner cannula shaft 24 may, in one embodiment, include an opening, or it can be a blunt, closed distal end. One skilled in the art will appreciate that the distal portion 44 of the inner cannula shaft 24 may have a variety of configurations suited to fit within the outer cannula assembly 12.

The outer diameter of the inner cannula shaft 24 is preferably of suitable dimensions such that it is able to fit within lumen 22 of the outer cannula assembly 16 in a relatively tight clearance fit. That is, while the inner cannula shaft 24 should be free to move relative to the outer cannula assembly 12, the spacing between the inner wall of cannula shaft 16 and the outer well of cannula shaft 24 should allow little or no fluid flow therethrough. The inner diameter of cannula shaft 24 should also be sufficient to allow transport of bone marrow and other fluids therethrough without damaging any blood cells. In an exemplary embodiment, the inner diameter of the inner cannula shaft 24 is in the range of about 1.0 mm to 3.5 mm.

The inner cannula assembly 14 further includes a proximal portion 42, which is adapted to mate with the proximal portion 32 of the outer cannula assembly 12, and which can connect to a suction device (not shown). Preferably, the proximal portion 42 of the inner cannula assembly 14 is generally cylindrical in shape. A distal most portion 50 is adapted to mate within the port 40 of the outer cannula assembly 12, preferably in an interlocking or interference fit. A person skilled in the art will appreciate that the proximal portions 42, 32 of the inner and outer cannula assemblies 14, 12 can be mated to one another using a variety of alternative techniques. The proximal portion 42 of the inner cannula assembly 14 also forms a handle-like device which facilitates grasping by a user to perform selective relative movement between the inner cannula assembly 14 and the outer cannula assembly 12. Such a handle may include any design which allows a user to grasp the proximal end 42 of the inner cannula assembly 12, such as the wing configuration 52 shown in FIG. 3.

The proximal portion 42 of the inner cannula assembly 14 also includes a connector portion 54 in fluid communication with the inner lumen 28 of the inner cannula assembly 14, and which is preferably adapted to mate with a suction source (not shown). The connector portion 54 can include threads 56, preferably formed on the outer surface thereof, for mating with a hose or with corresponding threads formed on a surgical syringe or similar medical device.

The device of the present invention may further include indicia 58 that signify where the openings 26, 20 on the inner cannula shaft 24 and the outer cannula shaft 16 are located, and that assists with aligning these openings. As shown in FIG. 2A, indicia 58 may be positioned on the proximal surface of both the inner cannula assembly 14 and the outer cannula assembly 12 so that a user can determine the radial location of the openings 26, 20. When the indicia 58 on the inner and outer cannulae are aligned, an opening 26 on the inner cannula 30 and an opening 20 on the outer cannula 14 will have the same radial position. Additional indicia may be positioned on the inner and the outer cannulae to confirm longitudinal alignment of the openings. The indicia may include grooves, colors, depressions, or any other feature used for marking.

The device of the invention can be used as follows. After appropriate patient preparation and anesthetization, the outer cannula assembly is inserted into a desired harvesting site. Prior to insertion, the inner cannula assembly can be mated with the outer cannula assembly to increase the strength and rigidity of the device, or alternatively, the assemblies can be mated following insertion. In either case, the inner cannula assembly may then be connected to a suction source. The inner cannula assembly is moved relative to the outer cannula assembly to align at least one opening in the outer cannula with at least one opening on the inner cannula, thus creating an active withdrawal aperture. Suction is then applied and the sample (e.g., bone marrow) is withdrawn through the withdrawal aperture until the supply is depleted adjacent that withdrawal aperture. The inner cannula is then moved relative to the outer cannula to align the at least one opening of the inner cannula with one or more different opening in the outer cannula to create a new withdrawal aperture. One skilled in the art will appreciate that the movement of the inner cannula can be translational movement, rotational movement, or a combination thereof. Such movements can be manually or automatically effected. For additional sampling locations, the outer cannula can be indexed by rotating it by a certain angle (e.g., 45°) and repeating the movement of the inner cannula to select the outer openings again.

In a further aspect of the invention, the device can be automated such that it can be equipped with a computer and/or electromechanical interface which electronically or electro-mechanically controls the selective relative movement between the inner and the outer cannulae. One skilled in the art will appreciate that feedback controls can be based on volume of sample withdrawn and/or the duration of withdrawal from any given withdrawal aperture.

In yet another embodiment of the present invention, the bone marrow sampling device 10' (FIGS. 5–7) further comprises a second inner cannula 60 disposed within the outer cannula assembly 12. The second inner cannula 60 may be positioned inside the inner cannula assembly 14, or alternatively the second inner cannula 60 may be disposed between the inner cannula assembly 14 and the outer cannula assembly 12. In either embodiment, the second inner cannula 60 provides additional freedom to control the opening and closing of withdrawal apertures. For example, a second inner cannula 60 may be particularly useful when the relative position of the first inner cannula 24 and the outer cannula 16 results in multiple withdrawal apertures, but the bone marrow cells adjacent to one of the withdrawal apertures have been depleted. Instead of withdrawing unwanted plasma through the unproductive withdrawal aperture during aspiration, the second inner cannula 60 may be positioned to block the unwanted withdrawal aperture.

With further reference to FIGS. 5–7, a bone marrow sampling device 10' is illustrated with a second inner cannula 60 positioned within the outer cannula assembly 12. In particular, the second inner cannula 60 is illustrated in FIGS. 5B and 5C as being positioned within the first inner cannula 24, and including proximal end 62 and distal end 64. In an exemplary embodiment, the second inner cannula 60 includes a cylindrical body sized to fit within the first inner cannula shaft 24, and a length which is less than that of the first inner cannula shaft 24. In a further embodiment, the second inner cannula 60 can have solid sidewalls and open proximal and distal ends. Alternatively, one of the proximal and distal ends of the second inner cannula 60 may be closed, such that when the second inner cannula is positioned within the first inner cannula, all aspiration from withdrawal apertures distal to the distal end of the second inner cannula 60 is blocked.

In use, the second inner cannula 60 is selectively movable with respect to the other cannula shafts 12, 14 such that the sidewall of the second inner cannula 60 can open or close at least one withdrawal aperture created between the first inner cannula 30 and the outer cannula 14. As shown in FIGS. 5(B) and (C), the second inner cannula 60 can be inserted into the proximal end of the first inner cannula assembly 24 and advanced in a longitudinal direction until the sidewall of the second inner cannula 60 blocks an unwanted withdrawal aperture. The withdrawal aperture can then be reopened by moving the second inner cannula longitudinally, or if the sidewall of the second inner cannula 60 has an opening 66, by moving the second inner cannula axially.

In another embodiment of the present invention, the device 10 can include a channel (not shown) in the wall of one of the cannula shafts for delivering treatment material to an area external to outer cannula assembly 12. The channel can be positioned in any of the cannulae, but in a preferred embodiment, the channel for delivering treatment fluid is found in the wall of the cannulae positioned immediately adjacent to the outer cannula assembly 12. In any case, the treatment material is preferably delivered to the sampling site to replace a sampled fluid and/or to promote healing. The treatment material can include saline, a drug and or a bioactive substance.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bone marrow sampling device, comprising:
   an outer cannula having a sidewall with an outer surface that forms the outer most exterior surface of the device, the sidewall defining an inner lumen and a closed distal end with a tissue penetrating tip, the sidewall having a plurality of openings formed at least at a distal portion of the outer cannula thereof, the openings being spaced apart at different radial and longitudinal positions on the sidewall, wherein each opening is in fluid communication with the inner lumen of the outer cannula;
   an inner cannula having a sidewall defining an inner lumen, the inner cannula being adapted to be disposed within and mated to the outer cannula such that the outer cannula and inner cannula are selectively moveable with respect to each other; and
   at least one opening formed in the sidewall of the inner cannula,
   wherein selective relative movement of the inner cannula and the outer cannula enables the device to be configured in multiple bone marrow sampling modes in which the at least one opening in the sidewall of the inner cannula is aligned with different openings in the sidewall of the outer cannula such that bone marrow can be drawn into the inner lumen of the inner cannula from different radial and longitudinal positions external to the sidewall of the outer cannula without the need to reposition the outer cannula.

2. The bone marrow sampling device of claim 1, wherein an alignment of the at least one opening in the inner cannula with one of the openings in the outer cannula creates a withdrawal aperture with a diameter in the range of about 0.5 mm to 3 mm.

3. The bone marrow sampling device of claim 1, wherein an alignment of the at least one opening in the inner cannula with one of the openings in the outer cannula creates a withdrawal aperture with an open surface area in the range of about 0.5 mm$^2$ to 8 mm$^2$.

4. The bone marrow sampling device of claim 1, wherein the outer cannula has a diameter in the range of about 0.7 mm to 6 mm.

5. The bone marrow sampling device of claim 1, wherein the inner cannula has a closed distal end.

6. The bone marrow sampling device of claim 1, wherein the inner cannula has a plurality of openings in the sidewall, each opening being spaced apart at different radial and longitudinal positions on the sidewall.

7. The bone marrow sampling device of claim 1, wherein the minimum distance between the openings in the sidewall of the outer cannula is at least about 5 mm.

8. The bone marrow sampling device of claim 1, wherein the selective relative movement between the inner cannula and the outer cannula is rotational movement.

9. The bone marrow sampling device of claim 1, wherein the selective relative movement between the inner cannula and the outer cannula is translational movement.

10. The bone marrow sampling device of claim 1, wherein the selective relative movement between the inner cannula and the outer cannula is a combination of rotational and translational movement.

11. The bone marrow sampling device of claim 1, wherein a proximal end of the inner cannula is adapted to mate with a suction device.

12. The bone marrow sampling device of claim 1, further comprising a second inner cannula disposed between the inner cannula and the outer cannula.

13. The bone marrow sampling device of claim 12, wherein the second inner cannula has a solid outer sidewall that is free of openings in the sidewall.

14. The bone marrow sampling device of claim 13, wherein the second inner cannula is selectively movable with respect to the inner cannula and the outer cannula, such that the selective movement of the second inner cannula blocks or opens at least one withdrawal aperture created between the inner cannula and the outer cannula by an alignment of the at least one opening in the inner cannula with one of the openings in the outer cannula.

15. The bone marrow sampling device of claim 12, wherein the second inner cannula has a channel formed in its outer sidewall, wherein the channel provides a passage for the deliver of a treatment material.

16. The bone marrow sampling device of claim 1, wherein the selective relative movement between the inner and outer cannula is automated.

17. The bone marrow sampling device of claim 1, wherein the openings formed in the outer cannula sidewall follow a helical pattern.

18. The bone marrow sampling device of claim 1, further comprising indicia formed on the inner cannula and the outer cannula to provide an indication when the at least one opening on the inner cannula lines up with one of the openings of the outer cannula to create a withdrawal aperture.

* * * * *